| United States Patent [19] | [11] Patent Number: 4,828,828 |
| Trager et al. | [45] Date of Patent: May 9, 1989 |

[54] METHOD OF TREATING DEGENERATIVE JOINT DISEASE BY INJECTION OF METH(ACRYLAMIDE) (CO)-POLYMERS

[76] Inventors: Seymour F. Trager, 14 Sherwood Dr., Plainview, N.Y. 11803; Victoria S. Chylinski, 11 Peghouse Rise, Slad Road, Stroud, Glos., England

[21] Appl. No.: 78,687

[22] Filed: Jul. 28, 1987

[51] Int. Cl.$^4$ .............................................. A61K 31/78
[52] U.S. Cl. ...................................... 424/81; 514/825
[58] Field of Search ........................... 424/81; 514/825

[56] References Cited

U.S. PATENT DOCUMENTS 3,697,653 10/1972 Ingley .................................. 514/825
3,975,516 8/1976 Hettinger, Jr. ....................... 424/81
4,312,866 1/1982 Caruso et al. ........................ 514/825

Primary Examiner—Joseph L. Schofer
Assistant Examiner—Peter F. Kulkosky
Attorney, Agent, or Firm—Fidelman & Wolffe

[57] ABSTRACT

A method for the treatment of degenerative joint disease in a mammal suffering therefrom which includes administration by injection of an effective amount of a pharmaceutical composition into the arthritically afflicted joints of the mammal thereby lubricating and cushioning the joints. The composition includes acrylamide or methacrylamide polymers or copolymers thereof having a molecular weight from about 1 to about 15 million and a pharmaceutically acceptable diluent.

12 Claims, No Drawings

METHOD OF TREATING DEGENERATIVE JOINT DISEASE BY INJECTION OF METH(ACRYLAMIDE) (CO)-POLYMERS

BACKGROUND OF THE INVENTION

Mammalian joints typically contain a small amount of synovial fluid which lubricates and moistens the joint surfaces to protect the joint against trauma, injury and degeneration. Some specific synovial fluid functions are to lubricate the joint surfaces, to absorb shocks to the joints, to bind acid and, possibly, to nourish some of the structural components of the joints. The synovial fluid is produced in the body by specialized cells, and the impairment of the fluid, i.e. decreased viscosity of the fluid due to the presence of degenerate cartilage products therein, is the principal source of the pain associated with degenerative joint diseases.

As a result, various modes of intra-articular treatment of arthritis have been proposed. Commercially available compositions including corticosteroids such as triamcinoline, prednisolone and hydrocortisone acetate are now in use in arthritis treatment. However, these compositions are difficult to use due to difficulties in dosage determination. Also, a number of adverse reactions have been observed in intra-articular steroid therapy. Consequently, corticosteroid treatments have fallen into relative disuse.

The use of hyaluronic acid has also been proposed for arthritis treatment. Hyaluronic acid appears to lubricate only the soft tissues of the joint which are not subject to heavy loading. Again, adverse side effects stemming from the treatment have been reported in some patients. Moreover, patients with clinical histories of local adverse reactions to the acid treatment appear susceptible to severe permanent joint damage.

Thus, there is interest in improved intra-articular treatments involving the injection of pseudo-synovial fluid into afflicted joints to replace or augment natural synovial fluid.

SUMMARY OF THE INVENTION

The present invention relates to a method of intra-articular treatment of degenerative joint disease in mammals involving the injection of a pseudo-synovial fluid composition comprising acrylamide or methacrylamide polymers or copolymers thereof into the afflicted joints of the mammals. The pseudo-synovial fluid composition serves to replace or augment the natural synovial fluid in the joints to protect it against wear and trauma and provides lubrication without inducing an inflammatory response. Moreover, the composition of the present invention is stable at room temperature and can be sterilized by boiling or autoclaving.

DETAILED DESCRIPTION OF THE INVENTION

The present invention involves a method for the treatment of degenerative joint disease in a mammal suffering therefrom through administration by injection of an effective amount of a pharmaceutical composition which comprises acrylamide or methacrylamide polymers or copolymers thereof having a molecular weight from about 1 to about 15 million and a pharmaceutically acceptable diluent into the arthritically afflicted joints of said mammal thereby lubricating and cushioning said joints.

The polyacrylamides effective in the process of the present invention are produced by the polymerization of acrylamide, methacrylamide or mixtures thereof by methods known in the art.

For example, the viscoelastic gel composition of the present invention can be formulated by autoclaving an 8–10% by weight solution of the polymer followed by admixture with a premixed sterile solution sufficient to obtain a final composition within the parameters of the present invention. The viscoelastic gel composition of the present invention can also be formulated by dispersion of the polymer in cold or warm water containing any additional ingredients desired for the final composition.

As a pharmaceutically acceptable diluent of the present invention, there is contemplated any biocompatible diluent which does not interfere with the anti-arthritic properties of the composition and is capable of suspension in gel form. Exemplary of such diluents are chloride salts, acetates, hydrates, quaternary amines, and other electrolytes such as acetic acid, sulfates, boric acid, nitrates, hydrochloric acid, phosphoric acid, hydroxides, phosphates and water.

The method of the present invention can be practiced on mammalian degenerative joint disease. Exemplary of degenerative joint diseases which may be treated using the composition of the present invention are the various forms of arthritis. Human and equine arthritis, for example, can be treated in this manner.

As an effective amount of the composition of the present invention, there is contemplated an amount sufficient to replace or augment natural synovial fluid to lubricate and cushion the afflicted joints. The exact dosage applied to an afflicted joint is a function of the joint involved, the severity of the degradation of the articulation and surrounding area, and the like. A typical dose can range from about 0.1 to about 10 ml of the composition of the present invention per injection. A preferred dose ranges from about 0.2 to about 5 ml of the composition of the present invention per injection.

The degenerative joint disease treatment may be accomplished through a single injection of the composition or a series dependent upon each individual clinical case. Further, should the symptoms of degenerative joint disease return, additional administrations can be used to alleviate these new symptoms.

A preferred embodiment of the present invention involves a method of administration of a pharmaceutical composition, wherein the polymers or copolymers preferably having a molecular weight on the order of about 5 million are present in an amount between about 2 to about 5 percent by weight of the pharmaceutical composition. A more preferred embodiment involves a method of administration of a pharmaceutical composition, wherein the polymers or copolymers are present in an amount between about 3.5 to about 5 percent by weight of the pharmaceutical composition, the most preferable being present in about 4.0 percent by weight.

Another preferred embodiment of the present invention involves a method of administration of a pharmaceutical composition, wherein the pharmaceutical composition has a Brookfield viscosity of about 30,000 to about 125,000 cps at 25° C. The pharmaceutical composition is a viscoelastic gel.

A further preferred embodiment of the present invention involves a method of administration of a pharmaceutical composition, wherein the pharmaceutical composition further comprises an antibiotic. Exemplary of such antibiotics are gentamycin sulphate, in a buffered alkaline form.

A further preferred embodiment of the present invention involves a method of administration of a pharmaceutical composition, wherein the pharmaceutical composition further comprises an anti-inflammatory agent. Exemplary of such anti-inflammatory agents are corticosteroids such as 6-methylprednisolone-21-acetate, 9-fluoro-prednisilone, triamcinolone acetate and the like. A preferred anti-inflammatory agent is 6-methyl-prednisolone-21-acetate.

An additional preferred embodiment of the present invention involves a method of administration of a pharmaceutical composition, wherein the pharmaceutical composition is administered in a dose from about 0.2 to about 5 ml.

When an antibiotic or anti-inflammatory agent is used in addition to the polymer or copolymer in the gel composition, a sufficient amount of the antibiotic or anti-inflammatory agent can be admixed with a sufficient amount of a gel composition prepared as described above to obtain a combination dosage form useful as a pseudo-synovial fluid. When an anti-inflammatory agent is utilized, an amount effective for anti-inflammatory use is contemplated. That is, a solution of about 1 ml to about 5 ml of the agent containing from about 5 to about 200 mg of anti-inflammatory agent is admixed with the gel composition. For example, the composition may contain from about 40 mg to about 200 mg of 6-methylprednisolone-21-acetate; from about 5 mg to 20 mg of 9-fluoro-predinisilone; 5 mg to 15 mg of triamcinolone acetate or mixtures thereof. When an antibiotic is used in the composition, an amount effective for antibiotic use is contemplated. For example, about 50 to about 200 mg gentamycin sulfate may be added to the composition to protect against infection.

Another preferred embodiment of the present invention involves a method of administration of a pharmaceutical composition, wherein the composition comprises (a) 2 to 5 percent by weight acrylamide or methacrylamide polymers or copolymers;

(b) 0.4 to 8.6 percent by weight sodium chloride;

(c) 0.075 to 0.3 percent by weight potassium chloride;

(d) 0.04 to 0.33 percent by weight calcium chloride;

(e) 0.02 to 0.04 percent by weight magnesium chloride hexahydrate;

(f) 0.3 to 0.4 percent by weight sodium acetate;

(g) 0.15 to 0.20 percent by weight buffering agent; and (h) remainder water.

As a buffering agent of the present invention, there is contemplated any pharmaceutically acceptable buffering agent. Exemplary of such buffering agents are citrate dihydrates such as sodium citrate dihydrate, phosphates such as sodium phosphates and borates such as sodium borate. The pH of the composition will preferably be in the alkaline range. The alkalinity of the composition will permit the gel to act as a buffer to protect the joint treated from the acid produced in the joint. Thus the acid damage to the joint will be decreased.

The method of the present invention involves the injection of a pharmaceutical composition into the afflicted joint area of the mammalian subject. Such injection may be accomplished through the use of a 19 or 20 gauge ×1 inch needle using sterile procedure.

Illustrative examples of the present invention are as follows.

Also, pharmaceutical compositions containing polymers or copolymers of acrylamide and methacrylamide polymers are known to be useful in opthalmic surgical and treatment procedures. See, for example, U.S. Pat. No. 4,540,568.

EXAMPLE 1

An autoclaved polyacrylamide having a molecular weight of about 5 million was admixed with a premixed salt solution to yield the following homogenous gel composition:

| Component | Percent by Weight |
|---|---|
| Polyacrylamide | 4.0 |
| Sodium chloride | 0.49 |
| Potassium chloride | 0.075 |
| Calcium chloride | 0.048 |
| Magnesium chloride hexahydrate | 0.030 |
| Sodium acetate | 0.390 |
| Sodium citrate dihydrate | 0.170 |
| Water | remainder |

EXAMPLE 2

An autoclaved polymethacrylate having a molecular weight of about 5 million was admixed with a premixed salt solution to yield the following homogenous gel composition:

| Component | Percent by Weight |
|---|---|
| Polyacrylamide | 4.0 |
| Sodium chloride | 0.49 |
| Potassium chloride | 0.075 |
| Calcium chloride | 0.048 |
| Magnesium chloride hexahydrate | 0.030 |
| Sodium acetate | 0.390 |
| Sodium citrate dihydrate | 0.170 |
| Water | remainder |

EXAMPLE 3

A 300 kg polyarthritic castrated male pony is treated with systemic tranquilization with 200 mg xylazine I.V. and manual restraint on both days of treatment.

A surgical clip (#40 blade) is placed over the dorsal aspect of both carpi and lateral aspect of both forelimb fetlocks. The sites are then prepped for surgery with betadine scrub and alcohol. Surgical gloves are used throughout the procedure.

5 ml synovial fluid is aspirated from the radiocarpal joints using a 19 G 1" needle and 6 cc syringe transferred to a Sodium Heparin tube. In a similar manner, 1.5 ml synovial fluid is removed from the forefetlocks. Using the needle already in place, 1.5 ml of the composition of Example 1 is injected into the afflicted joints.

No adverse reactions are noted with respect to lameness, heat, inflammation or swelling in the joints.

EXAMPLE 4

A 300 kg polyarthritic castrated male pony is treated with systemic tranquilization with 200 mg xylazine I.V. and manual restraint on both days of treatment.

A surgical clip (#40 blade) is placed over the dorsal aspect of both carpi and lateral aspect of both forelimb fetlocks. The sites are then prepped for surgery with betadine scrub and alcohol. Surgical gloves are used throughout the procedure.

5 ml synovial fluid is aspirated from the radiocarpal joints using a 19 G 1" needle and 6 cc syringe transferred to a Sodium Heparin tube. In a similar manner, 1.5 ml synovial fluid is removed from the forefetlocks. Using the needle already in place, 1.5 ml of the composition of Example 2 is injected into the afflicted joints.

No adverse reactions are noted with respect to lameness, heat, inflammation or swelling in the joints.

What is claimed is:

1. A method for the treatment of degenerative joint disease in a mammal suffering therefrom comprising administration by injection into the afflicted joints of said mammal of an effective amount of a pharmaceutical composition which comprises from about 2 to about 5 percent by weight acrylamide or methacrylamide polymers or copolymers thereof having a molecular weight from about 1 to about 15 million and a pharmaceutically acceptable diluent therefor, thereby lubricating and cushioning said joints.

2. A method of claim 1, wherein said polymers or copolymers are present in an amount between about 3.5 to about 5 percent by weight of said pharmaceutical composition.

3. A method of claim 1, wherein said polymers or copolymers are present in an amount of about 4 percent by weight of said pharmaceutical composition.

4. A method of claim 1, wherein said polymer is polyacrylamide.

5. A method of claim 1, wherein said pharmaceutical composition has a Brookfield viscosity of about 30,000 to about 125,000 cps at 25° C.

6. A method of claim 1, wherein said pharmaceutical composition further contains an antibiotic.

7. A method of claim 1, wherein said pharmaceutical composition further contains an anti-inflammatory agent.

8. A method of claim 7, wherein said anti-inflammatory agent is 6-methylprednisolone 21-acetate.

9. A method of claim 1 wherein said pharmaceutical composition is administered in a dose from about 0.2 to about 5 ml.

10. A method of claim 1, wherein said pharmaceutical composition comprises
    (a) 2 to 5 percent by weight acrylamide or methacrylamide polymers or copolymers;
    (b) 0.4 to 8.6 percent by weight sodium chloride;
    (c) 0.075 to 0.3 percent by weight potassium chloride;
    (d) 0.04 to 0.33 percent by weight calcium chloride;
    (e) 0.02 to 0.04 percent by weight magnesium chloride hexahydrate;
    (f) 0.3 to 0.4 percent by weight sodium acetate;
    (g) 0.15 to 0.20 percent by weight buffering agent; and
    (h) remainder water.

11. A method of claim 10 wherein said buffering agent is sodium citrate dihydrate.

12. A method of claim 1, wherein said pharmaceutical composition comprises about 4 percent by weight of said polymer having a molecular weight of about 5 million, about 0.49 percent by weight sodium chloride, about 0.075 percent by weight potassium chloride, about 0.048 percent by weight calcium chloride, about 0.03 percent by weight sodium citrate dihydrate and the remainder water.

* * * * *